United States Patent
Sawai et al.

(10) Patent No.: US 9,714,942 B2
(45) Date of Patent: *Jul. 25, 2017

(54) DETECTION METHOD AND DETERMINATION METHOD FOR DETECTION TARGET

(75) Inventors: Toshiya Sawai, Chiba (JP); Eri Oowada, Saitama (JP); Hirokazu Nagaoka, Ichihara (JP); Satoru Sugita, Matsudo (JP); Toshiya Ueki, Tokyo (JP)

(73) Assignees: JNC CORPORATION, Tokyo (JP); ORTHO-CLINICAL DIAGNOSTICS KABUSHIKI KAISHA, Tokyo (JP)

( * ) Notice: Subject to any disclaimer, the term of this patent is extended or adjusted under 35 U.S.C. 154(b) by 84 days.

This patent is subject to a terminal disclaimer.

(21) Appl. No.: 12/810,454

(22) PCT Filed: Dec. 25, 2008

(86) PCT No.: PCT/JP2008/073626
§ 371 (c)(1),
(2), (4) Date: Sep. 13, 2010

(87) PCT Pub. No.: WO2009/084596
PCT Pub. Date: Jul. 9, 2009

(65) Prior Publication Data
US 2010/0330688 A1 Dec. 30, 2010

(30) Foreign Application Priority Data
Dec. 28, 2007 (JP) .................................. 2007-339991

(51) Int. Cl.
*G01N 27/72* (2006.01)
*G01N 33/553* (2006.01)
(Continued)

(52) U.S. Cl.
CPC ..... *G01N 33/553* (2013.01); *G01N 33/54333* (2013.01); *G01N 33/54393* (2013.01)

(58) Field of Classification Search
CPC ........... G01N 33/54333; G01N 33/553; G01N 33/54393
(Continued)

(56) References Cited

U.S. PATENT DOCUMENTS 5,998,588 A * 12/1999 Hoffman et al. ............. 530/402
2003/0165962 A1 * 9/2003 Furukawa et al. ............... 435/6
(Continued)

FOREIGN PATENT DOCUMENTS

CA 2656203 A1 1/2008
EP 2037272 A1 3/2009
(Continued)

OTHER PUBLICATIONS

Hoffman A S et al. "Founder's Award, Society for Biomaterials. Sixth World Biomaterials Congress 2000, Kamuela, HI, May 15-20, 2000. Really smart bioconjugates of smart polymers and receptor proteins", Journal of Biomedical Materials Research vol. 52, No. 4, Dec. 15, 2000 (Dec. 15, 2000), pp. 577-586.
(Continued)

*Primary Examiner* — Rebecca M Fritchman
(74) *Attorney, Agent, or Firm* — Scully Scott Murphy & Presser

(57) ABSTRACT

It is intended to provide a detection method and a determination method for detection target capable of detecting and determining a detection target promptly and simply with high accuracy at low cost. The detection method includes the steps of: mixing a first conjugate 10 in which a first substance containing a stimulus-responsive polymer 11 and a particulate magnetic substance 19 is conjugated to a first antibody 13 against a detection target 50 with a sample;
(Continued)

applying a magnetic force after placing the resulting mixture in a condition capable of aggregating the stimulus-responsive polymer 11; measuring a generated magnetic field; and detecting the detection target 50 based on the degree of increase in the magnetic field after applying the magnetic force.

10 Claims, 9 Drawing Sheets

(51) Int. Cl.
*G01N 33/543* (2006.01)
*G01N 27/00* (2006.01)

(58) Field of Classification Search
USPC .............................. 436/86; 516/113; 977/840
See application file for complete search history.

(56) References Cited

U.S. PATENT DOCUMENTS

| | | | |
|---|---|---|---|
| 2004/0126899 A1 | 7/2004 | Lee et al. | |
| 2005/0113297 A1 | 5/2005 | Francois et al. | |
| 2006/0194887 A1* | 8/2006 | Kojima et al. ................ | 516/113 |
| 2008/0284413 A1* | 11/2008 | Tsukamoto ...... | G01N 33/54333 324/204 |

FOREIGN PATENT DOCUMENTS

| | | |
|---|---|---|
| JP | 58-11575 B2 | 3/1983 |
| JP | 2869684 B2 | 3/1999 |
| JP | 2927601 B2 | 7/1999 |
| JP | H11311625 A | 11/1999 |
| JP | 2000346844 A | 12/2000 |
| JP | 2002-85957 A | 3/2002 |
| JP | 2005082538 A | 3/2005 |
| JP | 3693979 B2 | 9/2005 |
| JP | 2006242597 A | 9/2006 |
| JP | 3845249 B2 | 11/2006 |
| JP | 2007071832 A | 3/2007 |
| JP | 3916330 B2 | 5/2007 |
| JP | 2007244374 A | 9/2007 |
| JP | 4071738 B2 | 4/2008 |
| WO | 9709068 A2 | 3/1997 |
| WO | 01/09141 A1 | 2/2001 |

OTHER PUBLICATIONS

Office Action for Canadian Patent Application No. 2710586 dated Oct. 23, 2012.
Office Action for Chinese Patent Application No. 200880123629.8 dated Nov. 29, 2012, with English translation.
Office Action for European Patent Application No. 08866922.1 dated Apr. 12, 2013.
Office Action for U.S. Appl. No. 12/810,038 dated Dec. 6, 2012.
Office Action for U.S. Appl. No. 12/810,038 dated Sep. 13, 2013.
Sahwath Jayagopal et al., "Surface Engineering of Quantum Dots for in Vivo Vascular Imaging" Bioconjugate Chem., 2007, 18: 1424-1433.
International Search Report for PCT/JP2008/073626, dated Jan. 21, 2009.
Wang et al., "Magnetically Responsive Fluorescent Polymer Particles", Patent Abstracts, 5395688, p. 565.
Extended European Search Report for European Application No. 08868061.6 mailed Nov. 30, 2010.
Chen et al., "Temperature-Responsive Magnetite/PEO-PPO-PEO Block Copolymer Nanoparticles for Controlled Drug Targeting Delivery", Langmuir: The ACS Journal of Surfaces and Colloids, vol. 23, No. 25, Dec. 4, 2007, pp. 12669-12676, XP002609574, ISSN: 0743-7463.
Furukawa et al., "Affinity selection of target cells from cell surface displayed libraries: a novel procedure using thermo-responsive magnetic nanoparticles", Applied Microbiology and Biotechnology, vol. 62, No. 5-6, Oct. 2003, pp. 478-483, XP002609573, ISSN: 0175-7598.
Haase, F., "HPLC Avidin Monomer Affinity Resin", Biotechnology Advances, Elsevier Publishing, vol. 13, No. 3, Jan. 1, 1995, p. 567, XP004045459, ISSN: 0734-9750.
Office Action issued to U.S. Appl. No. 12/306,178, mailed Apr. 22, 2011.
Furukawa et al., Affinity selection of target cells from cell surface displayed libraries: a novel procedure using thermo-responsive magnetic nanoparticles, 2003, Appl. Microbiol. Biotechnolog., 62, 478-483.
Data sheet ZZ domain, downloaded from the Internet [URL:http://www.ncbi.nlm.nih.gov/protein/2SPZ_A], printed on Apr. 9, 2011, p. 1.
Final Office Action issued to U.S. Appl. No. 12/306,178, mailed Dec. 6, 2011.
India Office Action, First Examination Report, for Coresponding Patent Application No. 2723/KOLNP/2010 dated Oct. 28, 2015.

* cited by examiner

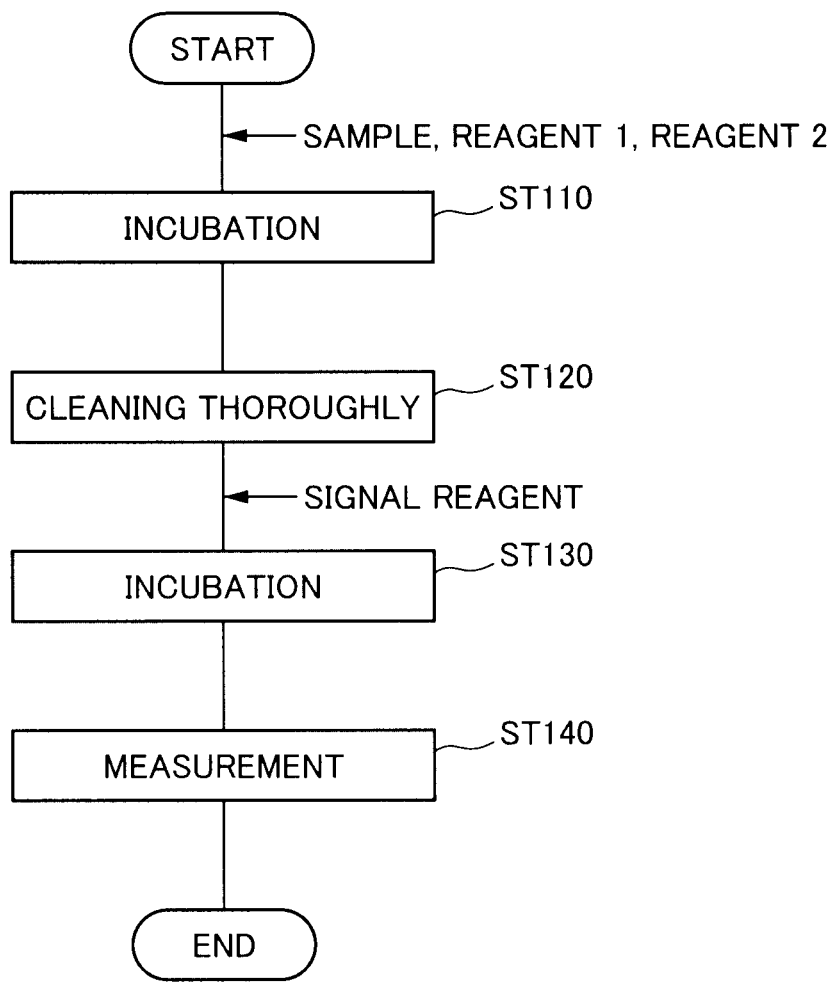

DETECTION METHOD AND DETERMINATION METHOD FOR DETECTION TARGET

CROSS-REFERENCE TO RELATED APPLICATIONS

This application is a National Stage of International Application No. PCT/JP2008/073626, filed Dec. 25, 2008, which claims the benefit of Japanese Application No. 2007-339991, filed Dec. 28, 2007, the contents of which are both incorporated by reference herein.

FIELD OF THE INVENTION

The present invention relates to a method for detecting and quantifying a target substance.

BACKGROUND OF THE INVENTION

The latex aggregation method has long been used for detecting a target substance in a sample. In the latex aggregation method, in order to detect an antigen present in liquid such as a biological sample, the liquid and latex carrying an antibody or a fragment thereof that specifically binds to the target antigen are mixed, and the degree of latex aggregation is measured to detect or quantify the antigen (e.g., Japanese Published Examined Patent Application No. S58-11575, hereinafter referred to as Patent Document 1).

According to the latex aggregation method, aggregation of latex is facilitated by an antigen, which is added as a sample and cross-links a plurality of latex-bound antibodies. This simple procedure allows for convenient and rapid detection of an antigen. However, when the amount of the antigen is small, since it is difficult to generate cross-linking, a sufficient amount of latex cannot aggregate. Therefore, it has been difficult to detect a small amount of antigen.

Thus, methods utilizing an enzyme-substrate reaction, such as ELISA and CLEIA, are widely adopted. In these methods, for example, a primary antibody that binds specifically to an antigen is bound to an antigen, and a secondary antibody having an enzyme is bound to this primary antibody. Then, an enzyme substrate is added and the reactivity of a reaction catalyzed by the enzyme is measured to detect or quantify an antigen.

According to these methods, by using a luminescent reagent as a substrate, for example, the high detectability of a luminous reaction after adding the substrate allows detection of a small amount of antigen.

SUMMARY OF THE INVENTION

Problems to be Solved by the Invention

However, the methods utilizing an enzyme-substrate reaction require a number of special reagents such as a secondary antibody and luminescent reagent, which make the operating cost high. Moreover, since the measuring process must be completed in an extremely short period of time to avoid color degradation (bleaching phenomenon) of the luminescent reagent, insufficiently accurate results are likely.

Meanwhile, as shown in FIG. 10, these methods consist of a plurality of steps that make the operation complex, such as incubation of the specimen and each reagent (ST110 and ST130), cleaning of the system (ST120), and detection of the luminous reaction (ST140). Each of these steps takes considerable time, and therefore these methods are not suitable for large-scale processing.

The present invention was developed in view of the abovementioned situation. An object of the present invention is to provide a method for detecting and quantifying a target substance that allows for rapid, inexpensive, convenient and highly sensitive detection and quantification of a target substance.

Means for Solving the Problems

The inventors found that aggregation of stimuli-responsive polymers is inhibited when an electrically charged substance or a hydrophilic substance is brought in close proximity thereto, and the degree of aggregation of stimuli-responsive polymers can be highly sensitively detected by applying a magnetic force, to accomplish the present invention. Specifically, the present invention provides the following.

In a first aspect of the present invention, a method for detecting a target substance in a sample is provided, including steps of mixing a first bound substance in which a first substance containing a stimuli-responsive polymer and a particulate magnetic material binds to a first affinity substance having affinity to the target substance, and a sample, placing a mixture thereof under predetermined condition to aggregate the stimuli-responsive polymer followed by applying a magnetic force thereto, and measuring the intensity of generated magnetic field to detect the target substance based on an increase in the intensity of the magnetic field after applying a magnetic force.

In a second aspect of the present invention, a method according to the first aspect further includes a step of adding the first substance to the mixture before applying a magnetic force.

In a third aspect of the present invention, a method according to the first aspect or the second aspect includes a step of mixing the first bound substance, the sample, and a second bound substance in which an electrically charged or hydrophilic second substance binds to a second affinity substance having affinity to the target substance, in which the first affinity substance and the second affinity substance can simultaneously bind to different sites of the target substance.

In a fourth aspect of the present invention, a method for quantifying a target substance in a sample is provided, including steps of: mixing a first bound substance in which a first substance containing a stimuli-responsive polymer and a particulate magnetic material binds to a first affinity substance having affinity to the target substance, and a sample, placing a mixture thereof under predetermined conditions to aggregate the stimuli-responsive polymer followed by applying a magnetic force thereto, measuring the intensity of generated magnetic field, and calculating the amount of the target substance in the sample based on a correlation equation between the amount of the target substance and the magnetic field under the predetermined conditions to aggregate.

In a fifth aspect of the present invention, a method according to the fourth aspect further includes a step of adding the first substance to the mixture before applying the magnetic force.

In a sixth aspect of the present invention, a method according to the fourth aspect or the fifth aspect includes a step of mixing the first bound substance, the sample, and a second bound substance in which an electrically charged or a hydrophilic second substance binds to a second affinity substance having affinity to the target substance, in which the first affinity substance and the second affinity substance can simultaneously bind to different sites of the target substance.

Effects of the Invention

According to the present invention, in the presence of a target substance, a first affinity substance binds to the target substance. Consequently, an electrically charged moiety or a hydrophilic moiety of the target substance is brought close to a stimuli-responsive polymer bound to the first affinity substance. Thus, the electrically charged moiety or the hydrophilic moiety is arranged in the vicinity of the stimuli-responsive polymer, whereby aggregation of the first substance by the stimuli-responsive polymer, in response to stimulation, is inhibited based on the amount of the target substance present.

When a magnetic force is applied to the first substance, in a case where the first substance is in a state of aggregation, the first substance exhibits ferromagnetism and displays significant remnant magnetism. On the other hand, in a case where the first substance is in a state of non-aggregation, the first substance exhibits superparamagnetism and does not display remnant magnetism. In other words, the extent of the increase in the intensity of the magnetic field after applying a magnetic force depends on the degree of aggregation of the first substance.

Thus, an increase in the intensity of the magnetic field after applying the magnetic force depends on the amount of the target substance, whereby the target substance can be detected based on an increase in the intensity of the magnetic field. Furthermore, the target substance can be quantified based on a correlation equation between the amount of the target substance and the magnetic field.

All of the abovementioned procedures can be conducted without particularly using any special reagent, and therefore are inexpensive and convenient. Additionally, the abovementioned procedure only measures the magnetic field and is not a system that utilizes a reaction catalyzed by an enzyme, and therefore the target substance can, with high sensitivity, be rapidly detected or quantified. In addition, the magnetic field to be measured is not significantly influenced by foreign substances in the sample, therefore, a pretreatment step for removing foreign substances prior to measurement is not necessarily required, and thus the target substance can, with high sensitivity, be rapidly detected or quantified.

BRIEF DESCRIPTION OF THE DRAWINGS

FIG. 10 is a flow chart of a method according to the conventional art.

EXPLANATION OF REFERENCE NUMERALS

Figure 1:
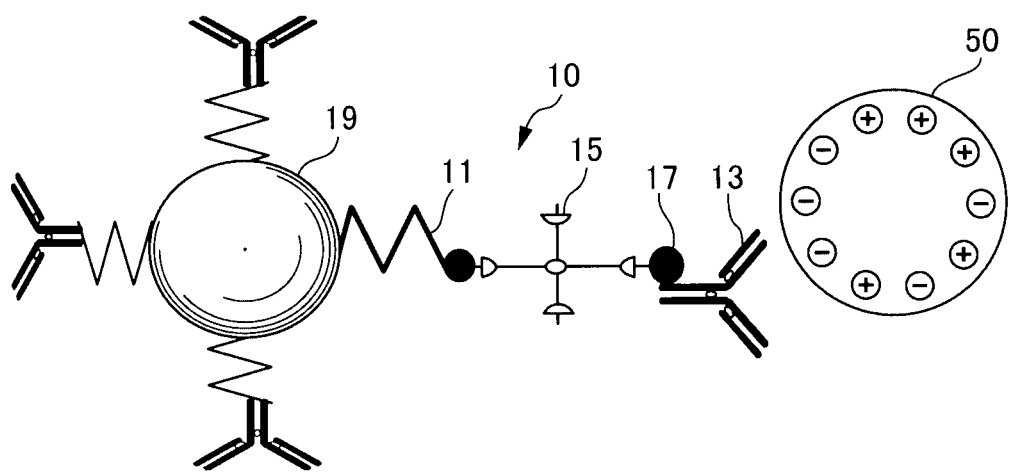
FIG. 1 is a schematic block diagram of the first bound substance used in a method according to an embodiment of the present invention.

10 First bound substance
11 Stimuli-responsive polymer
13 First antibody (first affinity substance)
15 Avidin
17 Biotin
19 Magnetic material
20 Second bound substance
21 Second substance
23 Second antibody (second affinity substance)
50 Target substance

DETAILED DESCRIPTION OF THE PREFERRED EMBODIMENTS

Embodiments of the present invention are explained with reference to diagrams below. Note that identical elements used in the first and subsequent embodiments are identified with identical numerals, and the respective descriptions contained within the description of the first embodiment have been omitted from the descriptions of subsequent embodiments.

First Embodiment: Detection Method

Mixing and Aggregation

In a method for detecting the target substance according to the present invention, firstly a first bound substance and a sample are mixed, and the mixture thereof is subsequently subjected to conditions to aggregate the stimuli-responsive polymer. Initially, the first bound substance used therein is described in detail.

First Bound Substance

The first bound substance is a substance in which a first substance containing a stimuli-responsive polymer binds to a first affinity substance having affinity to the target substance.

First Substance

The first substance used in the present invention contains a stimuli-responsive polymer which undergoes a structural change in response to an external stimulus, thereby being a polymer that can adjust the degree of aggregation and dispersion. The stimulus is not limited to a specific stimulus, temperature change, irradiation of light, addition of acid or base (change in pH) and electric field change can be used, for example.

Particularly, in the present invention, a temperature-responsive polymer, which is able to aggregate and disperse in response to temperature change, can be used as the stimuli-responsive polymer. The temperature-responsive polymer includes polymers which have a lower critical solution temperature (hereinafter referred to as LCST), and polymers which have an upper critical solution temperature (hereinafter referred to as UCST). For example, a polymer having a lower critical solution temperature with a LCST at 37° C. is completely dispersed in an aqueous solution with a temperature lower than LCST, and can be immediately aggregated by increasing the solution temperature to be higher than LCST. In addition, a polymer having an upper critical solution temperature with a UCST at 5° C. is completely dispersed in an aqueous solution with a temperature higher than UCST, and can be immediately aggregated by decreasing the solution temperature to be lower than UCST.

Polymers used in the present invention which have lower critical solution temperatures, include: polymers N-substituted (meth)acrylamide derivative such as N-n-propyl acrylamide, N-isopropyl acrylamide, N-ethyl acrylamide, N,N-dimethyl acrylamide, N-acryloyl pyrrolidine, N-acryloyl piperidine, N-acryloyl morpholine, N-n-propyl methacrylamide, N-isopropyl methacrylamide, N-ethyl methacrylamide, N,N-dimethyl methacrylamide, N-methacryloyl pyrrolidine, N-methacryloyl piperidine and N-methacryloyl morpholine; polyoxyethylene alkyl amine derivatives such as hydroxypropyl cellulose, polyvinyl alcohol partial acetal, polyvinylmethyl ether, (polyoxyethylene-polyoxypropylene) block copolymer, and polyoxyethylenelauryl amine; polyoxyethylenesorbitan ester derivatives such as polyoxyethylenesorbitanlaurate; (polyoxyethylenealkylphenyl ether)(meth)acrylates such as (polyoxyethylene nonylphenylether)acrylate, (polyoxyethyleneoctylphenylether)methacrylate; and polyoxyethylene(meth)acrylic ester derivatives such as (polyoxyethylene alkyl ether)(meth)acrylate of (polyoxyethylenelauryl ether)acrylate, (polyoxyethyleneoleyl ether)methacrylate. Furthermore, these polymers and copolymers having at least two unlike monomers of the above species can be used as well. In addition, a copolymer of N-isopropyl acrylamide and N-t-butyl acrylamide can also be used.

When a polymer having (meth) acrylamide derivative is used, the polymer can be copolymerized with other copolymerizable monomers, as long as the polymer has a lower critical solution temperature. Particularly, in the present invention, polymers having at least one monomer selected from the group consisting of N-n-propyl acrylamide, N-isopropyl acrylamide, N-ethyl acrylamide, N,N-dimethylacrylamide, N-acryloyl pyrrolidine, N-acryloyl piperidine, N-acryloyl morpholine, N-n-propyl methacrylamide, N-isopropyl methacrylamide, N-ethyl methacrylamide, N,N-dimethyl methacrylamide, N-methacryloyl pyrrolidine, N-methacryloyl piperidine, and N-methacryloyl morpholine, or a copolymer of N-isopropyl acrylamide and N-t-butyl acrylamide are preferably used.

Polymers having an upper critical solution temperature used in the present invention include polymers having at least one monomer selected from the group consisting of acryloyl glycineamide, acryloyl nipecotamide, acryloyl asparagineamide, and acryloyl glutamineamide, and the like. In addition, copolymers including at least two unlike monomers of these can be used as well. The abovementioned polymers can be copolymerized with other copolymerizable monomers such as acrylamide, acetyl acrylamide, biotinol acrylate, N-biotinyl-N'-methacryloyl trimethylene amide, acryloyl sarcosineamide, methacryl sarcosineamide, acryloyl methyluracil, etc. as long as the polymer has an upper critical solution temperature.

Additionally, in the present invention, a pH-responsive polymer which is able to aggregate and disperse by a change in pH can be used as the stimuli-responsive polymer. A pH at which a structural change of the pH-responsive polymer occurs is not limited to a particular pH, however, is preferably in the range of pH 4 to 10, more preferably in the range of pH 5 to 9, in order to prevent a decrease in the accuracy of detection/quantification due to denaturation and the like of the first bound substance, the second bound substance or the sample when the stimulus is applied.

The pH-responsive polymer includes polymers containing groups such as a carboxyl group, a phosphate group, a sulfonyl group, an amino group and the like as a functional group. More specifically, such pH-responsive polymer can be polymerized with monomers having a dissociable group, including: (meth)acrylic acid; maleic acid; styrenesulfonic acid; 2-acrylamide-2-methylpropanesulfonic acid; phosphoryl ethyl(meth)acrylate; amino ethyl methacrylate; aminopropyl(meth)acrylamide; and dimethylaminopropyl(meth) acrylamide. In addition, such pH-responsive polymer can be the abovementioned monomers having a dissociable group copolymerized with other vinyl monomers, by the degree that does not deteriorate the pH response: (meth)acrylic esters such as methyl(meth)acrylate, ethyl(meth)acrylate and butyl(meth)acrylate; vinyl esters such as vinyl acetate and vinyl propionate; vinyl compounds such as styrene, vinyl chloride, N-vinylpyrrolidone; and (meth)acrylamides.

Particulate Magnetic Material

The particulate magnetic material used in the present invention can be constituted of a multivalent alcohol and magnetite. Any multivalent alcohol can be used without limitation, provided that it has at least two hydroxyl groups in constitutional units and can bind to an iron ion, for example, dextran, polyvinyl alcohol, mannitol, sorbitol, and cyclodextrin. For example, Japanese Unexamined Patent Application No. 2005-82538 discloses a method for manufacturing particulate magnetic material using dextran. Alternatively, a compound such as glycidyl methacrylate polymer, which has an epoxy group and forms a multivalent alcohol structure after ring opening, can be used as well. The mean particle size of the particulate magnetic material (magnetic particles) prepared using multivalent alcohol is preferably in the range of 0.9 nm to 1000 nm, in order to ensure superior dispersion. Particularly for increased detectability of the target substance, the mean particle size is preferably at least 2.9 nm and less than 200 nm.

The first affinity substance may be a monoclonal antibody which recognizes the different antigenic determinants of the target substance. The antibody used herein can be any type of immunoglobulin molecule, for example an immunoglobulin molecule fragment which has an antigen binding site such as Fab. In addition, the antibody can be a monoclonal antibody or a polyclonal antibody.

Preparation of First Bound Substance

The first bound substance is prepared by binding the first substance and the first affinity substance. Though, the binding method is not limited to a particular method; for example, substances having affinity to each other (e.g., avidin and biotin, glutathione and glutathione S-transferase) are bound to the first substance (for example, a stimuli-responsive polymer moiety) and to the first affinity substance (for example, the first antibody), and the first substance and the first affinity substance are bound to each other via these substances.

Specifically, as described in the International Publication Pamphlet No. WO 01/009141, biotin can be bound to the stimuli-responsive polymer by binding biotin or other affinity substances to a polymerizing functional group such as methacryl or acryl to produce an addition polymerizable monomer, which further copolymerizes with other monomers. In addition, avidin or the other affinity substances can be bound to the first affinity substance by a common method. Then, by mixing a biotin-bound stimuli-responsive polymer and an avidin-bound first affinity substance, the first affinity substance and the stimuli-responsive polymer are bound to each other via binding between avidin and biotin.

As an alternative, during polymerization, a monomer having functional groups such as a carboxyl group, an amino group or an epoxy group can be copolymerized with another monomer, then an antibody affinity substance (e.g., melon gel, protein A, protein G, etc.) can be bound to the polymer via the functional group according to a method known in the art. The antibody affinity substance thus obtained can be bound to the first antibody, to obtain a first bound substance in which the stimuli-responsive polymer binds to the first antibody of the target antigen.

Alternatively, during polymerization, a monomer having functional groups such as a carboxyl group, an amino group or an epoxy group can be copolymerized with another monomer, then the first antibody for the target antigen can be bound directly to these functional groups according to a commonly known method.

Alternatively, the first affinity substance and the stimuli-responsive polymer can be bound to the particulate magnetic material.

The first bound substance can be purified by subjecting the first substance containing the stimuli-responsive polymer to a condition where the stimuli-responsive polymer aggregates, followed by separating the aggregated polymer by centrifugation. The first bound substance can also be purified by binding the particulate magnetic material, and then the first affinity substance to the stimuli-responsive polymer, followed by collecting the magnetic material by applying a magnetic force.

The particulate magnetic material and the stimuli-responsive polymer can be bound by a method well-known in the art, such as a method of binding via a reactive functional group, or a method to graft polymerize from an active hydrogen in a multivalent alcohol or from a polymerizable unsaturated bond introduced to a multivalent alcohol itself in the magnetic substance (See, ADV. Polym. Sci., Vol. 4, p. 111, 1965; J. Polymer Sci., Part-A, 3, p 1031, 1965).

The steps of the detection method are described again hereinafter. By subjecting a mixture of the above mentioned first bound substance and the sample to the conditions to aggregate the stimuli-responsive polymer, in a case where the target substance is present, aggregation of the stimuli-responsive polymer is inhibited by the electrically charged moiety or the hydrophilic moiety of the target substance, and the stimuli-responsive polymer disperses. On the other hand, in a case where the target substance is not present, the stimuli-responsive polymer aggregates, since aggregation is not inhibited.

This phenomenon is described with reference to FIGS. 1 and 2.

As shown in FIG. 1, a first bound substance 10 contains a stimuli-responsive polymer 11, and the stimuli-responsive polymer 11 is bound to a first antibody 13 for a target substance 50 via avidin 15 and biotin 17. Furthermore, the first bound substance 10 includes particulate magnetic material, and the stimuli-responsive polymer 11 is bound to the surface of this magnetic material 19. The target substance 50 can thus be brought close to the magnetic material 19 via the first antibody 13, and a positively charged moiety of the target substance 50 is located in the vicinity of the magnetic material 19. It should be noted that, although the positively charged moiety of the target substance 50 is located in the vicinity of the magnetic material 19 in the present embodiment, the present invention is not limited thereto. A negatively charged moiety or a hydrophilic moiety thereof can also be located in the vicinity of the magnetic material 19.

To aggregate the stimuli-responsive polymer 11, for example, in cases where a temperature-responsive polymer is used, a vessel containing the mixture can be moved to an incubator at an aggregation temperature of the temperature-responsive polymer. There are two types of the temperature-responsive polymers: a polymer having UCST and a polymer having LCST. For example, in a case where a polymer having a lower critical solution temperature with a LCST at 37° C. is used, the temperature-responsive polymer can be aggregated by placing the vessel containing the mixture in an incubator of no less than 37° C. In a case where a polymer having an upper critical solution temperature with a UCST at 5° C. is used, the temperature-responsive polymer can be aggregated by placing the vessel containing the mixture in an incubator of no greater than 5° C.

In addition, in a case where a pH-responsive polymer is used, an acid solution or an alkaline solution can be added to the vessel containing the mixture. Specifically, to a vessel containing a dispersed mixture with a pH in the range in which a structural change of the pH-responsive polymer does not occur, an acid solution or an alkaline solution can be added to change the pH of the dispersed mixture to the range in which a structural change of the pH-responsive polymer occurs. For example, in a case where a pH-responsive polymer, which aggregates at a pH of no greater than 5 and disperses at a pH greater than 5, is used, an acid solution can be added to the vessel containing the mixture that is dispersed at a pH greater than 5, to lower the pH to be no greater than 5. In addition, in a case where a pH-responsive polymer, which aggregates at a pH of no less than 10 and disperses at a pH of less than 10, is used, an alkaline solution can be added to the vessel containing the mixture that is dispersed at a pH less than 10, to raise the pH to be no less than 10. A pH at which a structural change of the pH-responsive polymer occurs is not limited to a particular pH; however, is preferably in the range of pH 4 to 10, more preferably in the range of pH 5 to 9.

Furthermore, in a case where a light-responsive polymer is used, the vessel containing the mixture can be irradiated with light having a wavelength that can aggregate the polymer. The preferred type of light depends on the type and structure of a light responsive functional group contained in the light-responsive polymer, however, generally ultraviolet radiation or visible radiation with a wavelength in the range of 190 to 800 nm can preferably be used. A luminous intensity thereof is preferably in the range of 0.1 to 1000 mW/cm2. For improved measurement accuracy, the light-responsive polymer is preferably not dispersed, in other words is preferably aggregated, by the irradiation of light for the measurement of turbidity. In a case where a light-responsive polymer is used which disperses upon irradiation of light used for the measurement of turbidity, accuracy of the measurement can be improved by shortening irradiation time.

Figure 2A:
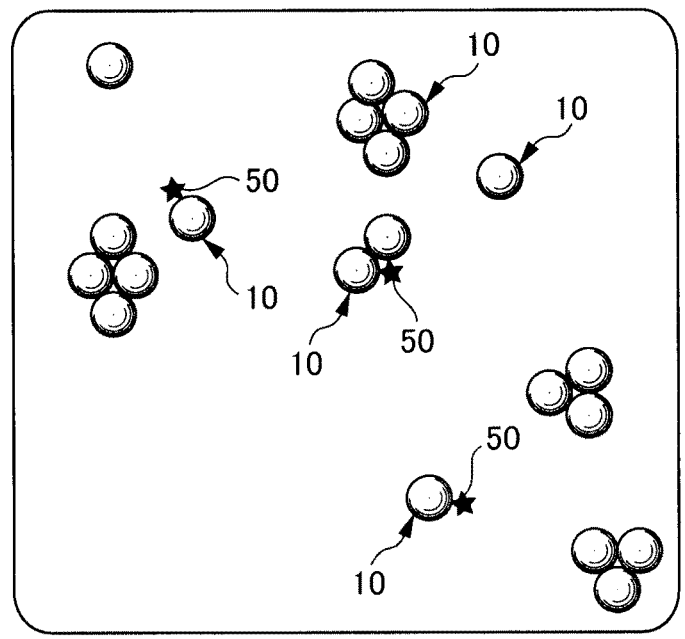
FIG. 2 is a schematic view showing a usage state of the first bound substance according to the embodiment of the present invention.
Figure 2B:
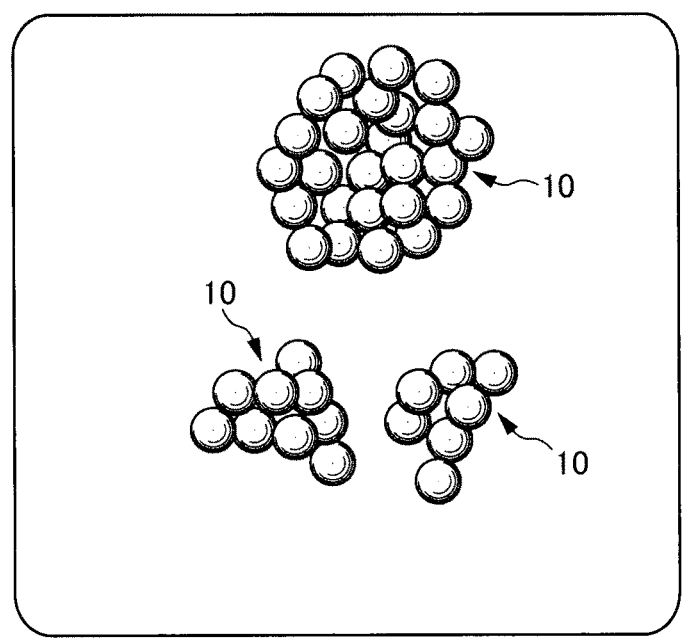

By subjecting the mixture of the first bound substance 10 and the sample to the abovementioned conditions, in cases where the target substance 50 is present, aggregation of the stimuli-responsive polymer 11 is inhibited by the positively charged moiety of the target substance 50, and the stimuli-responsive polymer disperses (FIG. 2A). On the other hand, in a case where the target substance 50 is not present, the stimuli-responsive polymer 11 aggregates since aggregation thereof is not inhibited (FIG. 2B).

Note that the aggregation of temperature-responsive polymer can take place after or simultaneously with binding of the first bound substance and the target substance; however, the latter is preferred so as to shorten the processing time.

Here, the lower critical solution temperature is determined as follows. To begin with, a sample is added to a cell of an absorptiometer, and heated at a rate of 1° C./min. During this period, the change in transmittance at 550 nm is recorded. The transmittance is 100% when the polymer is dissolved to be transparent, and 0% when completely aggregated. LCST is defined by determining the temperature where the transmittance is 50%.

For example, the upper critical solution temperature is determined as follows. The sample is cooled at a rate of 1° C./min. and the change in transmittance at 550 nm is recorded in the same way as in the case of the lower critical solution temperature. Transmittance is 100% when the polymer is dissolved to be transparent, and 0% when completely aggregated. UCST is defined by determining the temperature where the transmittance is 50%.

Application of a Magnetic Force/Measurement of a Magnetic Field

Application of a magnetic force and measurement of a magnetic field can be performed according to commonly known methods. One embodiment is described below, though the present invention is not limited thereto.

Figure 3:
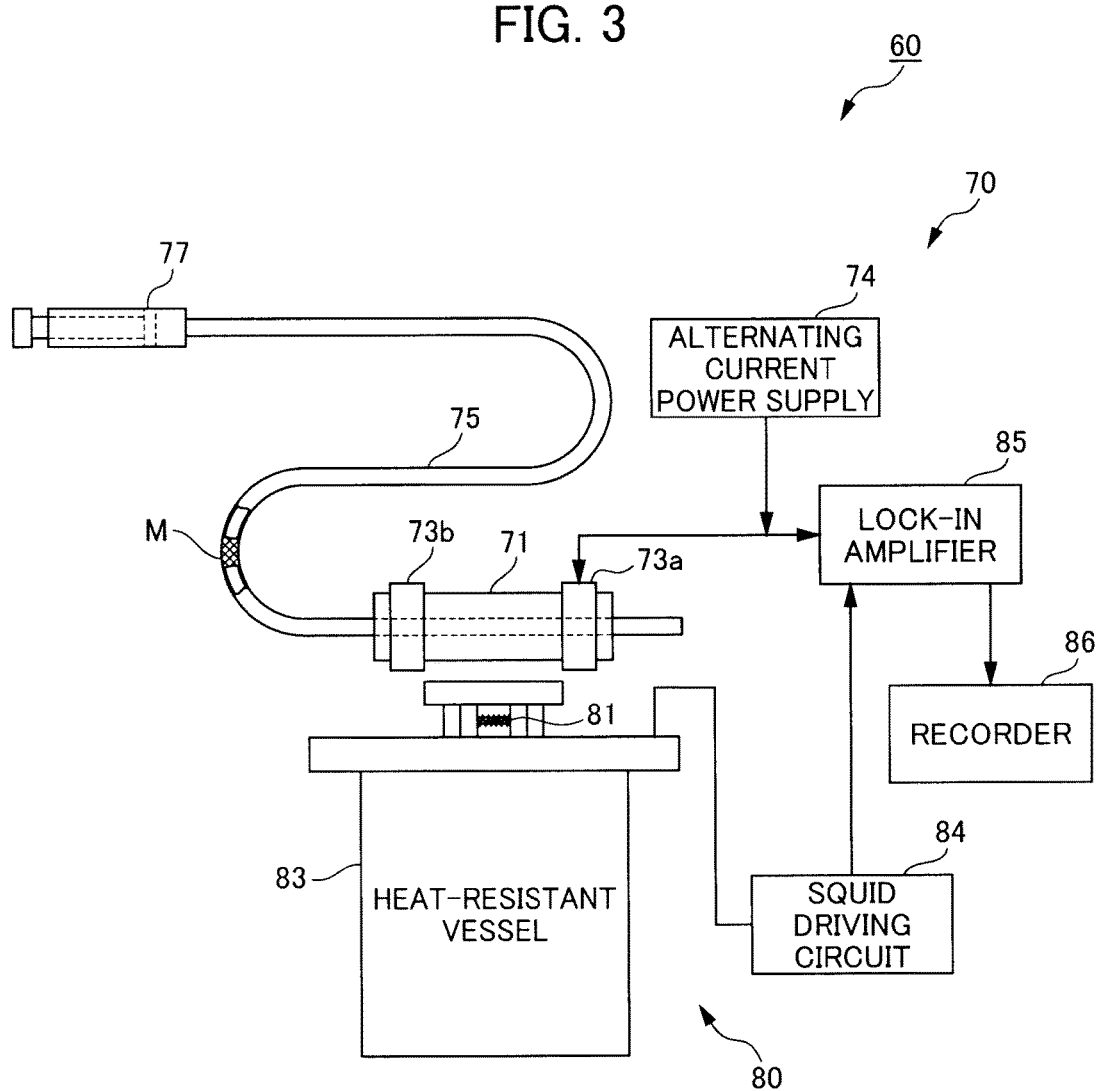
FIG. 3 is a schematic configuration diagram of a tester used in a method according to an embodiment of the present invention.

FIG. 3 is a schematic block diagram of tester 60. Tester 60 includes a magnetic force applying system 70 and a magnetic field measuring system 80.

Magnetic force applying system 70 includes a support pipe 71, inside which a sample tube 75 is inserted along the axial direction of the support pipe 71. A sample M extruded from a syringe pump 77 is transferred into the sample tube 75. Here, a sample M is a mixture of a first bound substance and a sample.

Helmholtz coils 73a and 73b are provided at both ends of the support pipe 71 in relation to the axial direction. Helmholtz coils 73a and 73b are electrically connected to an alternating current power supply 74, which supplies an alternating current to the helmholtz coils 73a and 73b to generate an alternating current magnetic field inside the support pipe 71. Thus, a sample M which was extruded into the support pipe 71 is transferred outside of the support pipe 71, after the magnetic force is applied.

The helmholtz coils 73a and 73b include a pair of cylinder coils of the same radius and the same winding number disposed separately along the axial direction and connected in series. Such a pair of coils is preferred in a case where a more uniform magnetic field is required compared to the magnetic field generated by a single coil. It should be noted that, in the present embodiment, the winding of both coils 73a and 73b are in the same direction, and the polar character of the generated magnetic field is the same.

A magnetic field measuring system 80 includes a SQUID magnetic sensor 81, which is set on a heat-resistant vessel 83. The SQUID (superconducting quantum interference device) is a superconducting ring having one or two Josephson junction, and is suitable for a high sensitivity magnetometer, a magnetic near-field antenna, and for measuring weak electrical current or electrical voltage. The magnetic sensor 81 is disposed at the lower portion of the support pipe 71, and receives a magnetic field generated by the sample M which passes through the inside of the magnetic sensor 81. At this time, if the target substance is present in the sample M, the first bound substance disperses, and the magnetic field does not increase significantly. On the other hand, if the target substance is not present in the sample M, the first bound substance aggregates, and the magnetic field increases significantly.

The magnetic sensor 81 transmits such a magnetic field signal to a SQUID driving circuit 84, then the SQUID driving circuit 84 converts the magnetic field signal to a voltage signal and transmits the signal to a lock-in amplifier 85. The voltage signal received by the lock-in amplifier 85 is amplified, and then, is output to a recorder 86.

By observing the change in the signal output to the recorder 86, in a case where significant increase of the signal strength is recognized, the target substance is determined not to be present in the sample, and in a case where a significant increase of the signal strength is not recognized, the target substance is determined to be present in the sample. Here, a range of "significant increase" is determined in advance, according to the condition of the system used for detection.

Target Substance

The target substance which can be detected with the abovementioned detection method includes substances used for clinical diagnosis such as, human immunoglobulin G, M, A and E, human albumin, human fibrinogen (fibrin and degradation product thereof), α-fetoprotein (AFP), C-reactive protein (CRP), myoglobin, carcinoembryonic antigen, hepatitis virus antigen, human chorionic gonadotropin (hCG), human placental lactogen (HPL), HIV antigen, allergen, bacterial toxin, bacterial antigen, enzyme, hormone (for example, human thyroid stimulating hormone (TSH) and insulin), and drugs that are contained in body fluid, urine, sputum, stool and the like.

Although there are many cases in which various and large quantities of foreign substances exist in a sample (blood, etc.) which are likely to contain the abovementioned target substances, a magnetic field measured is not significantly influenced by the foreign substances in the sample. Therefore, a pretreatment step for removing the foreign substances prior to measurement is not necessarily required.

Operation and Effect

According to the first embodiment of the present invention, the following operation and effect can be obtained.

In the presence of a target substance, a first affinity substance binds to the target substance. Consequently, an electrically charged moiety or a hydrophilic moiety of the target substance is brought close to a stimuli-responsive polymer bound to the first affinity substance. Thus, the electrically charged moiety or the hydrophilic moiety is arranged in the vicinity of the stimuli-responsive polymer, whereby aggregation of the first substance by the stimuli-responsive polymer, in response to stimulation, is inhibited based on the amount of the target substance present.

When the magnetic force is applied to the first substance, the first substance, when in an aggregated state, exhibits ferromagnetism and remnant magnetism; alternatively, when the first substance is in a non-aggregated state, it exhibits superparamagnetism and does not display remnant magnetism. In other words, an increase in the intensity of the magnetic field after applying a magnetic force depends on the degree of aggregation of the first substance.

Thus, an increase in the magnetic field after applying the magnetic force depends on the amount of the target substance, whereby the target substance can be detected based on an increase in the intensity of the magnetic field.

All of the abovementioned procedures can be conducted without particularly using any special reagent, and therefore are inexpensive and convenient. Furthermore, the abovementioned procedure only measures the magnetic field and is not a system that utilizes a reaction catalyzed by an enzyme, and therefore the target substance can, with high sensitivity, be rapidly detected. In addition, the magnetic field to be measured is not significantly influenced by foreign substances in the sample, therefore, a pretreatment step for removing foreign substances prior to measurement is not necessarily required, and thus the target substance in the whole blood sample and the like can, with high sensitivity, be rapidly detected.

Second Embodiment: Quantitative Method

In a quantitative method according to the present invention, to begin with a first bound substance and a sample are mixed, and the mixture thereof is subsequently subjected to predetermined conditions to aggregate the stimuli-responsive polymer aggregates, followed by applying the magnetic force. Then, the intensity of the generated magnetic field is measured, and an amount of a target substance in the sample is calculated based on a correlation equation between the amount of the target substance and the intensity of the magnetic field under the predetermined condition. An explanation is omitted for steps in the anterior half step of this method, which is similar to the aforementioned detection method.

Correlation Equation

The correlation equation between the amount of the target substance and the intensity of the magnetic field under the same conditions as the abovementioned predetermined conditions is constructed. Although, the measurement of the amount of the target substance and the intensity of the magnetic field, which forms the basis of the correlation equation, may be based on at least 2 samples containing different amounts, it is preferably based on at least 3 samples containing different amounts thereof, in respect of obtaining a highly reliable correlation equation.

The correlation equation between the amount of the target substance and the intensity of the magnetic force is not limited to an equation indicating a direct correlation between the amount of the target substance and the intensity of the magnetic force, and can be a correlation equation between the amount of the target substance and parameters reflecting the intensity of the magnetic force, such as electrical pressure.

Calculation

The amount of the target substance in a sample can be calculated by assigning the measured intensity of the magnetic field to the resulting correlation equation.

Operation and Effect

According to the second embodiment of the present invention, the following operation and effect can be obtained.

As in the first embodiment, the increase in the intensity of the magnetic field after the application of the magnetic force depends on the quantity of the target substance. Therefore, the quantity of the target substance can be determined by assigning the measured intensity of the magnetic field to a correlation equation between the target substance and the intensity of the magnetic field.

Furthermore, the abovementioned procedure can be inexpensively and conveniently performed, and the target substance can, with high sensitivity, be rapidly quantified. In addition, a pretreatment step for removing the foreign substances prior to measurement is not necessarily required, and thus the target substance in the whole blood sample and the like can, with high sensitivity, be rapidly detected.

Third Embodiment: Addition of the First Substance

The present embodiment is different from the first and the second aspect of the present invention in respect of including the step of further adding the first substance to the mixture before applying the magnetic force.

In other word, in a detection method according to the present invention, the mixture is subjected to conditions to aggregate the stimuli-responsive polymer, in a state that the first substance is further added to the mixture of the first bound substance and the sample. Subsequently, the first substance further aggregates to the aggregated substance of the first bound substance, and the size of the aggregated substance becomes larger. Then, by applying the magnetic force thereto, the aggregated substance is strongly magnetized, and displays stronger remnant magnetism.

It should be noted that, although the first substance is added to the mixture of the first bound substance and the sample, in the present embodiment, the present invention is not limited thereto, and the first bound substance, the sample, and the first substance may be added in any order. Furthermore, the first substance can be added individually or in the state of being conjugated with other substances, that is, the first affinity substance is bound to the first bound substance.

According to the present embodiment, in addition to the abovementioned embodiment, the following operation and effect can be obtained.

The first substance is further added to the first bound substance and the sample, whereby, the aggregate formed is enlarged. Thus, the stronger magnetic field is generated after applying the magnetic force, whereby, the difference corresponding to the amount of the target substance is detected with amplification. Therefore, the target substance can, with higher sensitivity, be detected or quantified.

Fourth Embodiment: Usage of the Second Bound Substance

The present embodiment is different from the abovementioned embodiment in respect of mixing the first bound substance, the sample and the second bound substance. Hereinafter, details are described.

Second Bound Substance

The second bound substance is a substance in which an electrically charged or hydrophilic second substance binds to a second affinity substance having affinity to the target substance.

Second Substance

The electrically charged second substance is an electrically charged polymer compound, preferably a polyanion or polycation. The polyanion indicates a substance which has a plurality of anion groups, and the polycation indicates a substance which has a plurality of cation groups. Examples of the polyanion include nucleic acids such as DNA and RNA. These nucleic acids have the property of a polyanion because they have a plurality of phosphodiester groups along the backbone of the nucleic acids. In addition, the polyanion includes a polypeptide containing many carboxyl groups (polypeptide consisting of amino acids such as glutamic acid and aspartic acid), polyacrylic acid, polymethacrylic acid, polymers including acrylic acid or methacrylic acid as a polymerization component, and polysaccharides such as carboxymethylcellulose, hyaluronic acid and heparin. On the other hand, examples of the polycation include polylysine, polyarginine, polyornithine, polyalkylamine, polyethyleneimine, and polypropyl ethyleneimine, and the like. The number of functional groups of the polyanion (carboxyl group) or the polycation (amino group) is preferably at least 25.

The hydrophilic second substance is, for example, a water-soluble polymer compound such as: polymers containing an ether bond such as polyethylene glycol, polypropylene glycol, polyethylene oxide and polypropylene oxide; polymers containing an alcoholic hydroxyl group such as polyvinyl alcohol; and water-soluble polysaccharides such as dextran, cyclodextrin, agarose and hydroxypropylcellulose.

Such electrically charged or hydrophilic substances can have a functional group and the like in the polymer chain or at the end of the polymer chain to bind the second affinity substance.

The Second Affinity Substance

The second affinity substance is a substance which can simultaneously bind to different sites of the target substance with the first affinity substance. For example, the first affinity substance and the second affinity substance may be a monoclonal antibody recognizing the different antigenic determinants of the target substance.

Preparation Method

The second bound substance is prepared by binding directly or indirectly the second substance and the second affinity substance. The binding method is not limited to a particular method; however, for example, substances having affinity to each other (e.g., avidin and biotin, glutathione and glutathione S-transferase) are bound to both of the second substance and the second affinity substance (for example, the second antibody), and the second substance and the second affinity substance are indirectly bound to each other via the affinity substances.

When the second substance and the second affinity substance are directly bound, they can be bound via a functional group, for example, when using a functional group, maleimide-thiol coupling as in the method of Ghosh et al., (Ghosh et al.: Bioconjugate Chem., 1, 71-76, 1990) can be used. Specifically, the following two methods can be adopted.

According to a first method, a mercapto group (sulfhydryl group) is introduced to the 5' end of the nucleic acid, and a maleimide group is introduced to the antibody by reacting 6-maleimide hexanoic acid succinimide ester (e.g., EMCS (trade name) manufactured by DOJINDO LABORATORIES) with the antibody. Next, the abovementioned two substances are bound to each other via the mercapto group and the maleimide group.

According to a second method, a mercapto group is introduced to the 5' end of the nucleic acid, in a similar way to the first method. Then, the mercapto group is introduced to the antibody while N,N-1,2-phenylene di-maleimide, a homo bi-functional reagent, reacts with this mercapto group to introduce a maleimide group to the 5' end of the nucleic acid. Next, the abovementioned two substances are bound to each other via the mercapto group and the maleimide group.

Other methods known in the art to introduce nucleic acid to a protein include methods, for example, described in Nucleic Acids Research Vol. 15, p. 5275 (1987) and Nucleic Acid Research Vol. 16, p. 3671 (1988). These techniques can be applied for binding nucleic acid and antibody.

According to Nucleic Acids Research Vol. 16, p. 3671 (1988), oligonucleotide reacts with cystamine, carbodiimide, and 1-methylimidazole to introduce a mercapto group to the hydroxyl group at the 5' end of the oligonucleotide. After purifying the oligonucleotide, to which the mercapto group is introduced, the oligonucleotide is reduced by using dithiothreitol. Subsequently, by adding 2,2'-dipyridyl disulfide, a pyridyl group is introduced to the 5' end of the oligonucleotide via disulfide bond. On the other hand, regarding the protein, a mercapto group is introduced by reacting iminothiolane. The oligonucleotide to which the pyridyl disulfide is introduced and the protein to which mercapto group is introduced are mixed to react the pyridyl group and mercapto group specifically in order to bind the protein and the oligonucleotide.

According to Nucleic Acids Research Vol. 15, p. 5275 (1987), an amino group is introduced to the 3' end of the oligonucleotide, and reacted with the dithio-bis-propionic acid-N-hydroxysuccinimide ester (abbreviated name: dithio-bis-propionyl-NHS), which is a homo bi-functional reagent. After the reaction, dithiothreitol is added to reduce the disulfide bond in the dithio-bis-propionyl-NHS molecule, then a mercapto group is introduced to the 3' end of the oligonucleotide. For treatment of the protein, a hetero bi-functional cross linking agent, as described in Japanese Unexamined Patent Application No. 5-48100, is used. First, the protein reacts with the hetero bi-functional cross-linking agent having a first reactive group (succinimide group) that can react with a functional group (e.g., amino group) in the protein and a second reactive group (e.g. maleimide group) that can react with mercapto group. Then, the second reactive group is introduced to the protein to obtain a protein reagent activated in advance. The resulting protein reagent is bound covalently to the mercapto group of thiolized polynucleotide.

When using a polyanion and polycation other than the nucleic acid, by introducing a mercapto group to the ends or the other parts thereof, a second bound substance can be prepared in a similar way to the above.

The steps of a detection method and a quantitative method are described again hereinafter. In a detection method or a quantitative method according to the present invention, abovementioned second bound substance is mixed with the first bound substance and a sample, and the mixture thereof is subsequently subjected to conditions to aggregate the stimuli-responsive polymer. Then, in a case where the target substance is present, aggregation of the stimuli-responsive polymer is inhibited by the electrically charged moiety of the second bound substance and disperses. On the other hand, in a case where the target substance is not present, the stimuli-responsive polymer aggregates since aggregation thereof is not inhibited. This phenomenon is described with reference to FIGS. 4 and 5.

Figure 4:
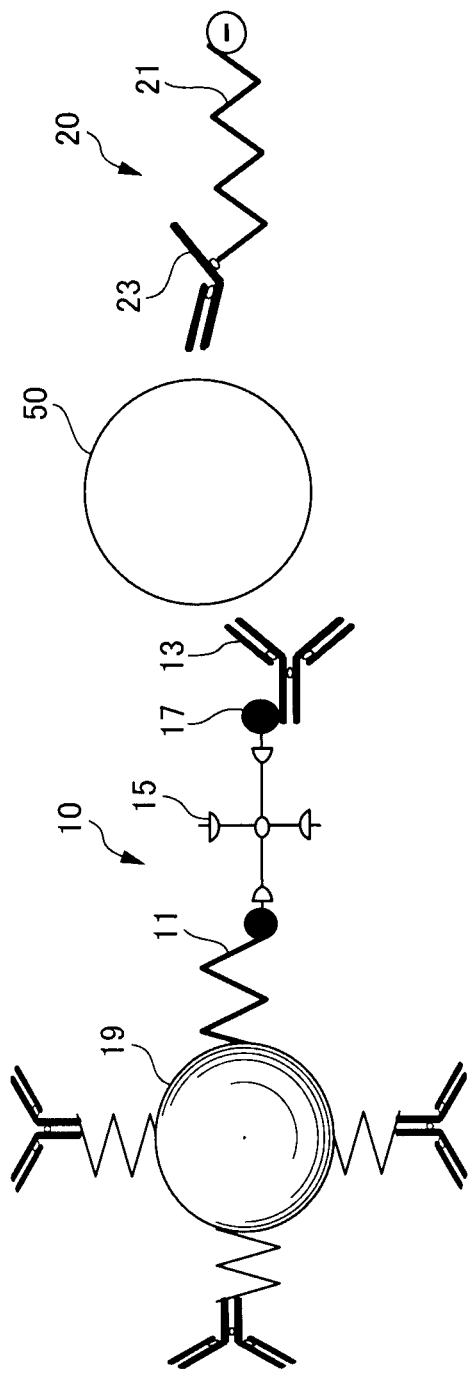
FIG. 4 is a schematic configuration diagram of the first bound substance and a second bound substance used in a method according to an embodiment of the present invention.

As shown in FIG. 4, a second bound substance 20 includes a negative charged or hydrophilic second substance 21, and the second substance 21 is bound to a second antibody 23 for target substance 50. Then, the first antibody 13 and second antibody 23 can be bound simultaneously to different sites of the target substance 50.

Figure 5A:
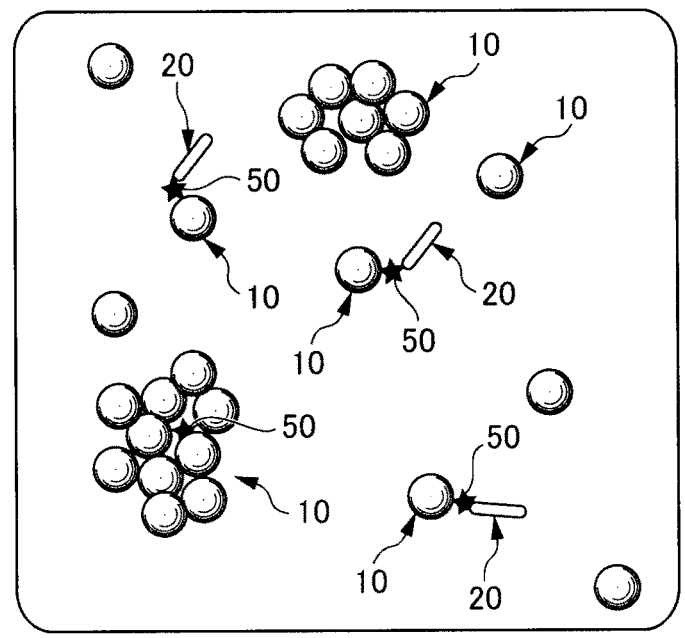
FIG. 5 is a schematic view showing a usage state of the first bound substance and the second bound substance according to the embodiment of the present invention.

As shown FIG. 5, by subjecting a mixture of the first bound substance 10, the second substance 20, and the sample to the predetermined conditions, in a case where the target substance is present, aggregation of the stimuli-responsive polymer is inhibited by the electrical charge or hydrophilic moiety of the second bound substance 20, and the stimuli-responsive polymer disperses (FIG. 5(A)). Here, the degree of the inhibition of aggregation of the first bound substance 10 is greater than the abovementioned embodiment (FIG. 2(A)).

Figure 5B:
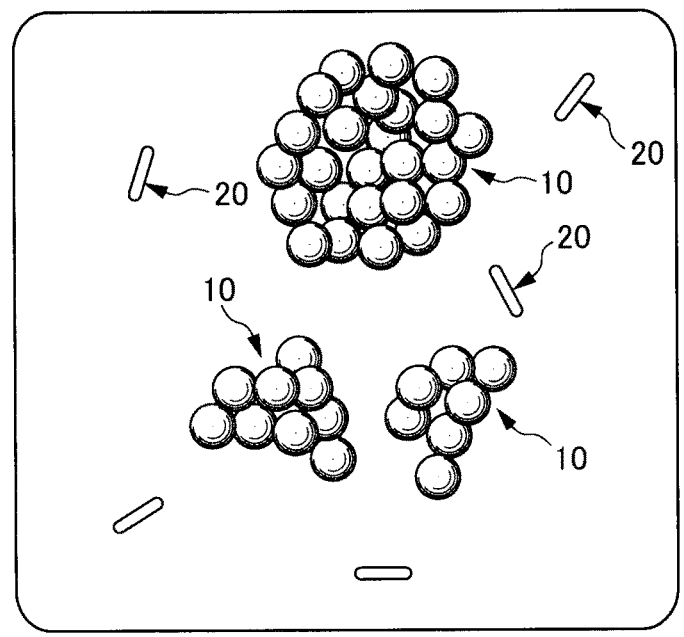

On the other hand, if the target substance 50 is not present, the stimuli-responsive polymer 11 aggregates since aggregation is not inhibited (FIG. 5(B)).

Note that aggregation of temperature-responsive polymer can take simultaneously with or after binding to the first bound substance and the second bound substance; the latter should be preferred due to shorter processing time. If aggregation conditions of the temperature-responsive polymer are greatly different from the conditions where the first bound substance and the second bound substance bind to a target substance, the former should be preferred.

According to the present embodiment, in addition to the abovementioned embodiment, the following operation and effect can be obtained.

If a target substance is present, a first affinity substance and a second affinity substance bind to the target. Therefore, a stimuli-responsive polymer bound to the first affinity substance and a second substance bound to the second affinity substance are brought close to each other. Thus, an electrically charged moiety or a hydrophilic moiety is arranged in the vicinity of a stimuli-responsive polymer. Therefore, aggregation of the stimuli-responsive polymer responding to stimulus is inhibited. Therefore, by observing the inhibition of aggregation, the presence or absence of the target substance can be detected. In addition, by measuring the degree of the inhibition of aggregation, the target substance can be quantified.

Consequently, the inhibition of aggregation depends on an electrically charged moiety or a hydrophilic moiety of the second substance, and the degree of dependence on the target substance is significantly decreased. Therefore, all target substances can be detected or quantified, and the accuracy and general versatility is improved.

Examples

The present Example exemplifies detection and quantification of glutathione (abbreviation: GSH) by using temperature-responsive polymer-surface modified magnetic particles including a protected thiol group (hereinafter also referred to as TM-LPDP) as the first bound substance, and N-hydroxysuccinimide-bound polyethylene glycol (hereinafter also referred to as NHS-PEG) SUN BRIGHT ME-400CS (manufactured by NOF CORPORATION, with average molecular weight 40000) as the second bound substance.

Representative reagents used in Examples of the present invention are as follows: PBS buffer: commercially available PBS at a 10× concentration (8.1 mM Na2HPO4, 1.5 mM KH2PO4, 2.7 mM KCl, 137 mM NaCl, pH 7.4, manufactured by Nippon Gene Co., Ltd.) diluted to 1/10 (V/V) with purified water; Borate buffer solution: Borate buffer manufactured by Polysciences, Inc., 100 mM Boric acid, pH 8.5; and purified water: water purified by Direct-Q (trade name) manufactured by Millipore Corporation.

Preparation of First Bound Substance

Therma-Max LAm Amine (0.4 mass %) manufactured by Magnabeat Inc. (hereinafter referred to as TM-LAm) was used as the amino group-bound temperature-responsive polymer-surface modified magnetic particles. 2 mL of TM-LAm was placed into a 2 mL microtube and heated to 42° C. to aggregate the TM-LAm. The aggregated substance was subsequently collected using a magnet, and the supernatant was removed. After removing the supernatant, 2 mL of borate buffer solution was added thereto to substitute a solvent thereof and sufficiently disperse TM-LAm. Borate buffer solution containing magnetic particles was thus obtained.

Subsequently, 2 mg of N-succinimidyl-3-(2-pyridyldithio)propionate (manufactured by Dojindo Laboratories, SPDP) dissolved in 100 μL of dimethyl sulfoxide was mixed with the borate buffer solution containing magnetic particles, and stirred overnight at 20° C. The stirred liquid was heated to 42° C. The aggregated substance was subsequently collected using a magnet, and the supernatant was removed. After removing the supernatant, 2 mL of PBS buffer was added to sufficiently disperse the aggregated substance. The abovementioned washing was repeated twice, thereby removing unreacted SPDP. The dispersed liquid was reheated to 42° C., the aggregated substance was collected using a magnet, and the supernatant was removed. Thereafter, the temperature-responsive polymer-surface modified magnetic particles including a protected thiol group was dispersed in PBS buffer, thereby preparing the first bound substance (particle content: 0.3 mass %).

Quantification of Glutathione Using Temperature-Responsive Polymer-Surface Modified Magnetic Particles Including a Protected Thiol Group and N-Hydroxysuccinimide-Bound Polyethylene Glycol Preparation of Sample Reduced glutathione (manufactured by Wako Pure Chemical Industries, Ltd.) was dissolved in a notably chylous specimen (Scan #: 1228761) of human normal serum manufactured by Pro MedDx LLC (10 Commerce Way North, Mass. 02766), so as to obtain samples of 12 μg/mL and 6 μg/mL, and a sample not containing glutathione.

Quantification

Mixing

500 μL of the above-described PBS buffer containing first bound substance was placed into a 1.5 mL tube and 10 μL of 0.5 M EDTA solution (pH 8, manufactured by Nippon Gene Co., Ltd.) was added thereto and mixed, thereby preparing a solution. 200 μL of the above each sample was added thereto and stirred for 12 hours at 4° C. Then 700 μL (200 μM) of NHS-PEG or PEG was added into the tube and stirred for 24 hours at 4° C. Thereafter, 800 μL of PBS buffer was added to 400 μL of the stirred substance, thereby obtaining a mixture.

Construction of Correlation Equation 1

A neodymium permanent magnet 73 (manufactured by NeoMag Co., Ltd.) of 5 mm×9 mm×2 mm was attached outside the optical path of a conventional semi-micro spectrophotometer cell. The cell was installed in an ultraviolet-visible spectrophotometer V-660DS (manufactured by JASCO Corporation) provided with a cell temperature control unit, and held for at least 10 minutes at 37° C.

The abovementioned mixture was dispensed into the cell, and after zeroing the spectrophotometer according to the instruction manual thereof, was immediately and continually measured for 1000 seconds, using a beam of light with a wavelength of 420 nm and a band width of 2.0 nm. The results are shown in FIG. 6.

Figure 6:
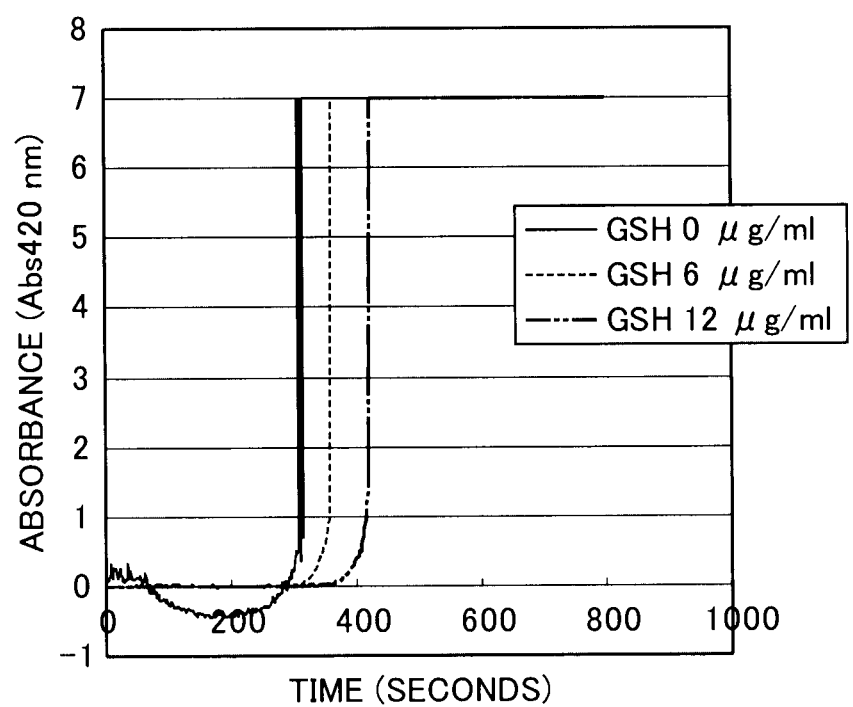
FIG. 6 is a graph showing a relationship between measurement time and turbidity in a method according to a reference example.

As shown in FIG. 6, absorbance of all the samples exceeded the detection limits in a small amount of time and was unmeasurable. Therefore, it was confirmed that, in a case with a sample that is naturally of high turbidity, such as the chylous specimen, quantification of a target substance by turbidity is difficult.

Construction of Correlation Equation 2

Figure 7:
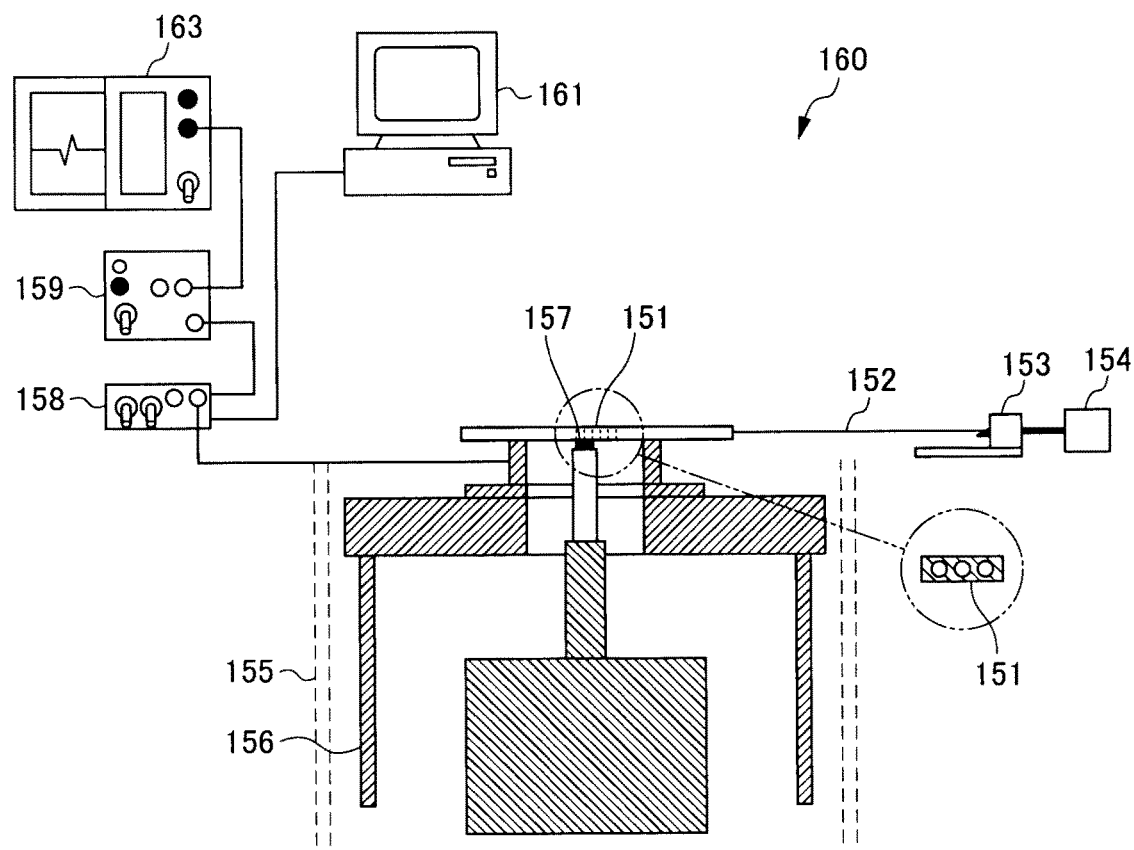
FIG. 7 is a schematic configuration diagram of a measuring device used in a method according to an embodiment of the present invention.

FIG. 7 is a schematic diagram of a measuring system 160 used in the present example. It should be noted that an AC magnetic field application device for the magnetic field applied to the sample is omitted. In FIG. 7, 151 is a slide substrate on which a sample is loaded, 152 is a wire, 153 is a driving motor, 154 is a control device, 155 is a cryostat (low-temperature preservation container), 156 is a magnetic shield box, 157 is a SQUID (ultrasensitive) magnetic sensor disposed above the cryostat (low-temperature preservation container) 155 and in the vicinity of the slide substrate 151, 158 is a driving circuit, 159 is an amplifier, 161 is a personal computer, and 163 is an X-Y pen recorder.

The measuring system 160 is constituted of: (1) the SQUID (ultrasensitive) magnetic sensor 157 for measuring a magnetic signal from temperature responsive magnetic nano particles, and the driving circuit 158; (2) the cryostat (low-temperature preservation container) 155 for maintaining the SQUID (ultrasensitive) magnetic sensor 157 at a low temperature; (3) a substrate transfer mechanism comprising the driving motor 153, the wire 152, and the control device 154; (4) the magnetic shield box 156 for shielding against magnetic noise such as geomagnetism; and the like. The driving circuit 158 is used for lowering noise.

90 µL of the abovementioned mixture was dispensed into polystylene well plates (cylindrical containers of 11 mm in height, 8 mm in diameter, and 0.5 mm in thickness of bottom), and then 90 µL of PBS buffer was added thereto and mixed. Each well plate was placed on a magnet Daruma Magutacchi (manufactured by Velos Co., Ltd.) in an incubator at 37° C. and left at rest for 3.5 minutes (magnetic separation).

Figure 8:
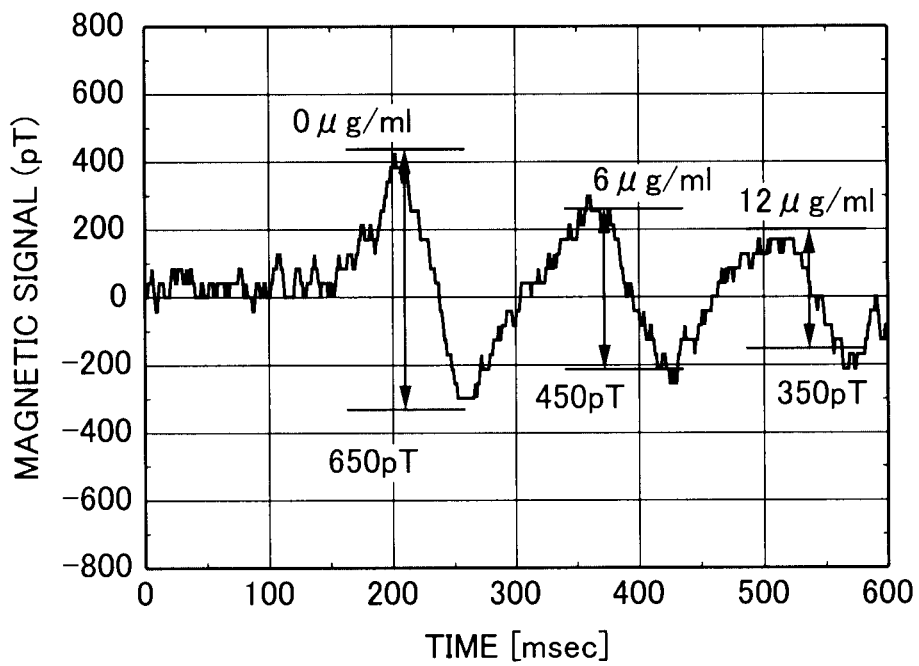
FIG. 8 is a graph showing a relationship between measurement time and intensity of magnetic field in a method according to the embodiment.

Subsequently, each well plate was loaded on the slide substrate 151 and transferred to a position right above the SQUID (ultrasensitive) magnetic sensor 157 by the transfer mechanism disposed outside the magnetic shield box 156. A magnetic signal was measured and recorded at the moment where each well plate passed through the magnetic sensor 157. The results thereof are shown in FIG. 8 (wherein a vertical axis represents flux as the magnetic signal). It should be noted that the measurement was conducted by an AC magnetic field method where the magnetic signal is measured by the SQUID magnetic sensor while an AC magnetic field is applied to the sample by a Helmholtz coil. In addition, an excitation magnetic field was 88 µT, an excitation frequency was 100 Hz, a sample transfer speed was 10 mm/sec, and a lift-off (distance between the SQUID magnetic sensor 157 and the sample) was 1 mm.

As shown in FIG. 8, measured values of the magnetic signal were very different in accordance with glutathione content, which is a target substance. It was thus confirmed that a target substance can be detected with a high degree of accuracy even with a specimen in which the target substance is difficult to detect by measuring turbidity (FIG. 6), such as a high-turbidity chylous specimen of serum sample. Therefore, the method of the present example is found to be able to detect a target substance with a high degree of accuracy in a wide range of whole-blood samples.

The first bound substance, the second bound substance and the samples were stored in the dark at 4° C. and the magnetic signal was measured in the same procedure once a day for three days. A graph showing a correlation equation between glutathione content and average of the magnetic signal (pT) is shown in FIG. 9.

Figure 9:
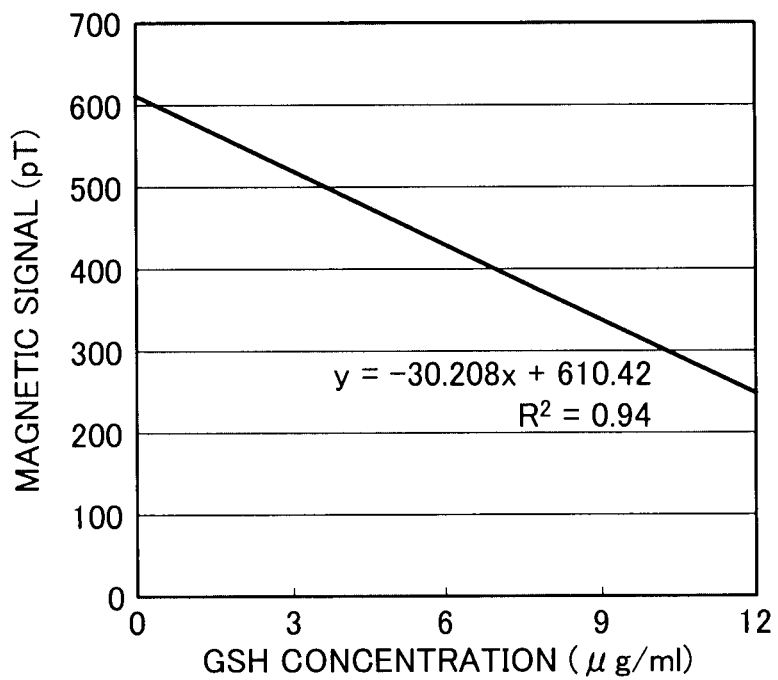
FIG. 9 is a graph showing a correlation equation between amount of a target substance and intensity of magnetic field in a method according to the embodiment.

As shown in FIG. 9, the correlation equation obtained was y=−30.208x+610.42 (wherein x is amount of glutathione and y is the magnetic signal). In addition, correlation coefficient R2 was 0.94, which is extremely high, and thus it was confirmed that a target substance can be quantified with a high degree of accuracy by this correlation equation, even with a specimen in which the target substance is difficult to detect by measuring turbidity, such as a chylous specimen.

The present invention is not limited to the above described embodiments. Accordingly, variations, improvements, and other modifications are included in the scope of the present invention without departing from the spirit or scope of the present invention. Although a stimuli-responsive polymer is necessarily used in the present invention, the invention is not limited to polymers, and a stimuli-responsive low-molecular-weight compound can also be used. Such a low-molecular-weight compound includes those disclosed in Japanese Patent Publication No. 3693979, Japanese Patent Publication No. 3916330, Japanese Unexamined Patent Application Publication No. 2002-85957, Japanese Patent Publication No. 4071738, Japanese Patent Publication No. 2869684, Japanese Patent Publication No. 2927601, Japanese Patent Publication No. 3845249, Japanese Unexamined Patent Application Publication No. 2006-242597, and the like.

What is claimed is:

1. A method for detecting in a sample a target substance comprising an electrically charged moiety or a hydrophilic moiety, comprising:
    i) mixing the sample with a first bound substance, said first bound substance comprising a stimuli-responsive polymer, a particulate magnetic material, and a first affinity substance, wherein said particulate magnetic material binds to said stimuli-responsive polymer and binds to said first affinity substance, said first affinity substance having affinity to the target substance, and wherein aggregation of said stimuli-responsive polymer is inhibited when the electrically charged moiety or the hydrophilic moiety of said target substance is brought into close proximity to said stimuli-responsive polymer by binding said first affinity substance to said target substance, and wherein the stimuli-responsive polymer aggregates if the target is not bound;
    ii) placing said sample and first bound substance under predetermined conditions to aggregate the stimuli-responsive polymer followed by
    iii) applying a magnetic force thereto; and
    iv) measuring an increase in the intensity of generated magnetic field as compared to the intensity of the magnetic field before applying the magnetic force, and detecting the target substance based on an amount of the increase in the intensity of the magnetic field, wherein in a case where the increase is detected, the target substance is determined not to be present in the sample, and in a case where an increase is not detected, the target substance is determined to be present in the sample.

2. The method according to claim 1, further comprising a step of: adding the stimuli-responsive polymer before applying a magnetic force.

3. The method according to claim 2, further comprising a step of: mixing the first bound substance, the sample, and a second bound substance in which an electrically charged or hydrophilic second substance binds to a second affinity substance having affinity to the target substance, wherein the first affinity substance and the second affinity substance can simultaneously bind to different sites of the target substance.

4. A method for quantifying in a sample a target substance comprising an electrically charged moiety or a hydrophilic moiety, comprising:
    mixing the sample with a first bound substance, said first bound substance a stimuli-responsive polymer, a particulate magnetic material, and a first affinity substance having affinity to the target substance, wherein said particulate magnetic material binds to said stimuli-responsive polymer and binds to said first affinity substance, and aggregation of said stimuli-responsive polymer is inhibited when the electrically charged moiety or the hydrophilic moiety of said target substance is brought into close proximity to said stimuli-responsive polymer by binding said first affinity substance to said target substance, and wherein the stimuli-responsive polymer aggregates if the target is not bound;

placing a mixture thereof under predetermined conditions to aggregate the stimuli-responsive polymer;

applying a magnetic force thereto;

measuring an increase in the intensity of generated magnetic field as compared to the intensity of the magnetic field before applying the magnetic force, wherein in a case where an increase in the intensity of the generated magnetic field is detected, the target substance is determined not to be present in the sample, and in a case where an increase in the intensity of the generated magnetic field is not detected, the target substance is determined to be present in the sample;

and calculating the amount of the target substance in the sample based on a correlation equation between the amount of the target substance and the magnetic field under the predetermined conditions.

5. The method according to claim 4, further comprising: adding the stimuli-responsive polymer to the mixture before applying the magnetic force.

6. The method according to claim 5, further comprising: mixing the first bound substance, the sample, and a second bound substance in which an electrically charged or hydrophilic second substance binds to a second affinity substance having affinity to the target substance, wherein the first affinity substance and the second affinity substance can simultaneously bind to different sites of the target substance.

7. The method according to claim 4, further comprising: mixing the first bound substance, the sample, and a second bound substance in which an electrically charged or hydrophilic second substance binds to a second affinity substance having affinity to the target substance, wherein the first affinity substance and the second affinity substance can simultaneously bind to different sites of the target substance.

8. The method according to claim 1, further comprising: mixing the first bound substance, the sample, and a second bound substance in which an electrically charged or hydrophilic second substance binds to a second affinity substance having affinity to the target substance, wherein the first affinity substance and the second affinity substance can simultaneously bind to different sites of the target substance.

9. The method according to claim 1, wherein the method does not comprises a pretreatment step for removing the foreign substances prior to the measurement of the intensity of generated magnetic field.

10. The method according to claim 4, wherein the method does not comprise a pretreatment step for removing the foreign substances prior to the measurement of the intensity of generated magnetic field.

\* \* \* \* \*